United States Patent [19]
Takak et al.

[11] Patent Number: 4,812,443
[45] Date of Patent: Mar. 14, 1989

[54] METHODS FOR ENHANCING DIFFERENTIATION AND PROLIFERATION OF HEMATOPOIETIC PROGENITOR CELLS

[75] Inventors: Fumimaro Takak; Akio Urabe, both of Tokyo; Michiya Shimamura, Funabashi; Masao Mizuno, Kurashiki, all of Japan

[73] Assignee: Kuraray Co., Ltd., Okayama, Japan

[21] Appl. No.: 748,403

[22] Filed: Jun. 24, 1985

[30] Foreign Application Priority Data

Jun. 29, 1984 [JP] Japan ................................ 59-132945

[51] Int. Cl.⁴ ............................................ A61K 31/66
[52] U.S. Cl. ................................................... 514/143
[58] Field of Search ........................................ 514/143

[56] References Cited
PUBLICATIONS

Pennock et al., Nature, vol. 186, pp. 470–472 (1960).
Burgos et al., Biochem. Journal, vol. 88, pp. 470–482 (1963).
Kennan et al., Biochem. Journal, vol. 165, pp. 405–408 (1977).
Carson et al., Proc. Natl. Acad. Sci. U.S.A., vol. 76, pp. 5709–5713 (1979).
Carson et al., J. Biological Chemistry, vol. 256, pp. 4679–4686 (1981).
Potter et al., Biochem. Biophys. Res. Comm., vol. 106, pp. 691–696 (1982).
Potter et al., Journal of Biological Chemistry, vol. 256, pp. 2371–2376 (1981).

Primary Examiner—Stanley J. Friedman
Attorney, Agent, or Firm—Wenderoth, Lind & Ponack

[57] ABSTRACT

A medicament containing a compound of the formula

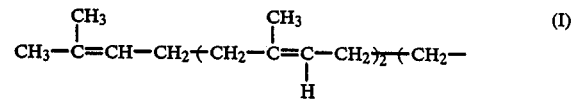

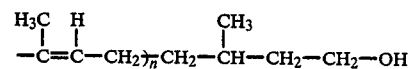

wherein

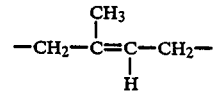

is a trans-isoprene unit,

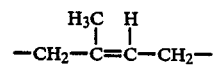

is a cis-isoprene unit, and n is an integer of from 12 to 18, or a pharmaceutically acceptable ester thereof.

The medicament is useful for the treatment of anemia, particularly aplastic anemia.

8 Claims, No Drawings

METHODS FOR ENHANCING DIFFERENTIATION AND PROLIFERATION OF HEMATOPOIETIC PROGENITOR CELLS

This invention relates to the use of dolichol or its ester in medicines. More specifically, it relates to a medicament or pharmaceutical composition especially useful for enhancing differentiation and proliferation of hematopoietic progenitor cells. Such a medicament or pharmaceuticalcomposition for enhancing differentiation and proliferation of hematopoietic progenitor cells is useful, for example, for the prevention, treatment or therapy of aplastic anemia in mammals including humans.

With an increase in aged population in recent years, various geriatric or geratic diseases have increased, and countermeasures against such diseases have become important. In particular, it has been strongly desired to develop drugs capable of promoting the differentiation and proliferation of hematopoietic progenitor cells for the therapy and treatment of geriatric anemia attributed to a decrease in hematopoiesis, impediment of hematopoiesis attributed to the administration of carcinostatic drugs or radioactive irradiation for cancer therapy, etc. Furthermore, in bone narrow transplantation devised as a method of treating these diseases, it has been considered effective to promote engraftment of the transplanted bone marrow cells by the use of suitable drugs that enhance differentiation and proliferation of hematopoietic progenitor cells. Thus, drugs having such a function have been desired.

It is well known that the differentiation and proliferation of hematopoietic progenitor cells are directly regulated by hematopoietic stimulating hormones such as erythropoietin (EPO) or colony stimulating factor (CSF). Various attempts have been actively made to promote differentiation and proliferation of hematopoietic progenitor cells by the administration of such hematopoietic stimulating hormones for the purpose of therapy of the hematopoietic disorders described above. However, these hormones are limited in their promoting activities and at present cannot be applied clinically to all of the aforesaid purposes. On the other hand, a series of in vitro studies on hematopoietic progenitor cells have demonstrated that various hormones such as shown in Table 1 affect erythropoiesis.

TABLE 1

| Effects of various hormones on colony formation of erythropoietic progenitor cells | |
|---|---|
| Adrenergic agonists | ↑ |
| Androgen | ↑ |
| cAMP (cyclic adenosine-monophosphate) | ↑ |
| Dexamethasone | ↑ |
| Estrogen | — |
| Growth hormone | ↑ |
| Human chorionic gonadotropin | — |
| Human chorionic somatomammotropin | ↑ |
| Progesterone | ± |
| Prolactin | — |
| Prostaglandin E | ↑ |
| Prostaglandin F | — |
| Thyroid hormone | ↑ |

[Quoted from M. J. Murphy, Jr. eds. In Vitro Aspects of Erythopoiesis, New York, Springer-Verlag, 81-85 (1978)]

Table 1 summarizes the results of evaluation of the effects of the various substances on colony formation of erythropoietic progenitor cells in an in vitro cell culture system. This method determines to what degree these substances increase the ability of hematopoietic progenitor cells to differentiation and proliferate in the presence of hematopoietic stimulating hormones, and is frequently used as a preliminary assay of substances affecting hematopoiesis for their clinical applications. It has been confirmed that a group of substances which show a positive (↑) effect in Table 1 are also effective on in vivo erythropoiesis.

Dolichol was first isolated in 1960 from human kidneys and the porcine liver by J. F. Pennock et al. [see Nature (London), 186, 470 (1960)]. Later, they ascertained that the dolichol is a mixture of polyprenol homologs having the following formula

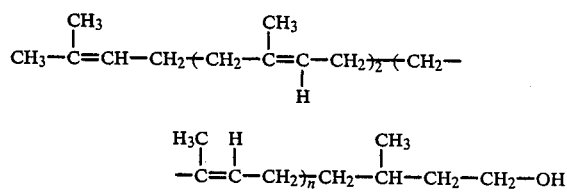

wherein

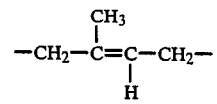

represents a trans-isoprene unit, and

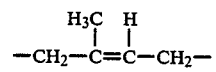

represents a cis-isoprene unit (the same definitions apply throughout the specification), and the number n of cis-isoprene units in the above formula generally distributes between 12 and 18 and three homologs in which n is 14, 15 and 16 are present in major proportions [see J. Burgos et al., Biochem. Journal, 88, 470 (1963) for the molecular structure; and R. W. Keenan et al., Biochem. Journal, 165, 405 (1977) for the distribution of the homologs].

It is known that dolichol distributes widely in mammals, and performs an important function in maintaining the lives of organisms. Particularly, it plays an important role in the formation of sugar chains in glycoprotein synthesis. For example, W. J. Lennarz et al. observed that the rate of dolichol biosynthesis in sea urchin embryos was activated during gastrulation which is a differentiation phenomenon of the embryos, and that the contents of dolichol in the embryos increased markedly. They also found that the aforesaid differentiation of sea urchin embryos did not occur when compactin, an inhibitor of dolichol biosynthesis, was added to the culture of the embryos. Based on these observations, they suggested that the differentiation of sea urchin embryos is closely related to the presence of dolichol [Proc. National Academy of Science, U.S.A., 76, 5709 (1979); and J. Biological Chemistry, 256, 4679 (1981)].

A. A. Kandutsch et al. observed that the rate of dolichol biosynthesis in spleen greatly increased during accelerated erythropoiesis attributed to anemia induced by subcutaneous administration of phenylhydrazine in mice and during accelerated erythropoiesis induced by intraperitoneal administration of erythropoietin in mice, and suggested close relationships between dolichol and erythropoiesis [Biochem. Res. Comm., 106, 691 (1982); and Journal of Biological Chemistry, 256, 2371 (1981)].

It has been extremely difficult to secure large quantities of dolichol because it has been available only by extraction from animal organs. Accordingly, the pharmacological and biological effects of the exogenous addition of dolichol have hardly been investigated. No study has been made as to what phenomena would be observed if dolichol is added to the aforesaid hematopoietic system.

The substances shown in Table 1 which have a promoting effect on colony formation of erythropoietic progenitor cells have an excellent erythropoiesis promoting effect, but are well known to have several physiologically strong effects in addition to such a promoting effect. For example, the adrenergic agonists cannot be used as agents for promoting differentiation and proliferation of hematopoietic progenitor cells because they act generally on the adrenergic system and induce great physiological impediments. Steroid hormones such as androgen and dexamethasone also have physiologically strong activities and cause clinically undesirable side-effects such as electrolytic disorders, hypertension, peptic ulcer, diabetes, liver impediments, and masculinization. Hence, full considerations and care are required in clinically using such steroid hormones. Since no other suitable drug exists, these steroid hormones are clinically used with care taken about their side-effects.

As stated above, in spite of the strong desire for drugs having the function of promoting the differentiation and proliferation of hematopoietic progenitor cells from a clinical viewpoint, there have been few effective compounds, or even those having the desired effects cannot be used because of their strong side effects, or they are used very carefully with full considerations to their side effects.

It is an object of this invention to provide a medicine having the function of effectively promoting differentiation and proliferation of hematopoietic progenitor cells without inducing such great side effects.

According to this invention, the above object is achieved by a medicament or pharmaceutical composition comprising as an active ingredient a compound represented by the following formula body of a mammal, the value n of dolichol represented by formula (I) distributes between 12 and 18. When the compound of formula (I) is to be used as an active ingredient in the present invention, the active ingredient may be a mixture of the compounds of formula (I) in which n distributes in nearly the same way as in vivo, or may be a mixture of two or more compounds of formula (I) in any desired ratios. As required, compounds of formula (I) may be isolated according to molecular weight and individually used as an active ingredient. Isolation of the individual compounds of different molecular weights may be effected by silica gel column chromatography as described in the above-cited EP-A-No. 0054753.

In the case of the mixture, the distribution of n in the compounds of formula (I) is desirably within the range shown in Table 2. The parenthesized figures show typical ranges.

TABLE 2

| n in formula (I) | Content (wt. %*) |
| --- | --- |
| 12 | 0–6 (0.1–6) |
| 13 | 4–17 (5–14) |
| 14 | 20–35 (23–32) |
| 15 | 30–50 (32–47) |
| 16 | 10–25 (11–20) |
| 17 | 2–10 (2–6) |
| 18 | 0–5 (0.1–2) |

*based on the weight of the mixture

It is more desirable that in such a mixture, the total proportion of the three compounds of formula (I) where n is 14, 15 and 16 is at least 70% by weight, preferably at least 75% by weight, based on the weight of the mixture.

Suitable pharmaceutically acceptable esters of the compounds of formula (I) include, for example, esters with lower fatty acids such as acetic acid and propionic acid; esters with higher fatty acids such as palmitic acid, oleic acid and stearic acid; and esters with phosphoric acid and monomannosyl phosphate. The esters with phosphoric acid are preferred. These esters can be synthesized in accordance with conventional methods of esterifying higher alcohols [L. L. Danilov and T. Chojnacki, Febs Letters, 131, 310 (1981); EP-A-No. 0054753; and Japanese Laid-Open Patent Publication No.

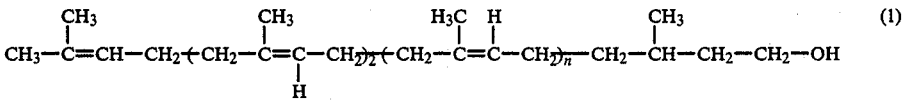

(I)

wherein n represents an integer of 12 to 18, or a pharmaceutically acceptable ester thereof.

The compound of formula (I) (namely, "dolichol") can be extracted from organs of mammals as stated above [J. Burgos et al., Biochem. Journal, 88, 470 (1963); and R. W. Keenan et al., Biochem. Journal, 165, 405 (1977)], and is also commercially available from Sigma Chemical Co., U.S.A. Preferably, it can be synthesized in pure form in large quantities by $C_5$ extension of polyprenyl fractions extracted from the leaves of plants such as *Ginkgo biloba* or *Cedrus deodara* in accordance with the method previously invented by one of the present inventors and his coworkers and described, for example, in European Patent Application Published Specification (EP-A) No. 0054753 published on June 30, 1982 (for specific synthesis procedures, see Referential Examples 1 and 2 given hereinbelow). Within the 62599/1984]. For example, reaction of dolichol with acetic anhydride in the presence of pyridine in hexane solvent can easily give dolichyl acetate. For more specific procedures, see Referential Examples 3 to 5 given hereinbelow.

The compounds of formula (I) and their pharmaceutically acceptable esters (to be generically referred to as "dolichols" unless otherwise stated) have an action of promoting differentiation and proliferation of hematopoietic progenitor cells in bone marrows of humans or animals, and are useful as drugs which enhance the hematopoietic function of humans or animals.

Generally, blood cells are produced in bone marrows, and its mechanism has been elucidated profoundly in recent years, and methods of assaying the differentiation and proliferation of various hematopoietic progenitor cells in a cell culture have been established [D. Metcalf, eds. Hematopoietic Colonies, Berlin, Springer-Verlag, 12-35 (1977)]. With regard to erythropoiesis, two progenitor cells in different differentiation stages, namely early erythrocytic progenitor cells (BFU-e) and late erythrocytic progenitor cells (CFU-e), are defined. In an in vitro cell culture system, BFU-e and CFU-e each differentiate and proliferate under the stimulation of erythropoietin, which is an erythropoietic stimulating hormone, to form a clonal colony of erythroblasts that synthesize hemoglobin. In the present invention, it has been found that the differentiation and proliferation of BFU-e and CFU-e are significantly enhanced by the exogenous addition of the dolichols into the cell culture system.

On the other hand, with regard to leucopoiesis, it is known that granulocyte-macrophage progenitor cells (CFU-c) differentiate and proliferate under the stimulation of colony stimulating factor (CSF), which is a leucopoietic stimulating hormone, to form a clonal colony of granulocytes or macrophages, in an in vitro cell culture system. It has now been also found that the addition of the dolichols to the cell culture system significantly enhances differentiation and proliferation of CFU-c.

The dolichols thus have effects of enhancing differentiation and proliferation of hematopoietic progenitor cells, and supplementing and increasing the hematopoiesis promoting effect of hematopoiesis stimulating hormones and are considered to be very useful drugs for enhancing differentiation and proliferation of hematopoietic progenitor cells.

The aforesaid activity of the dolichols to enhance differentiation and proliferation of hematopoietic progenitor cells can be demonstrated by the following in vitro or in vivo experiments.

The mouse bone marrow cells used in the following experiments were all prepared as follows:

BDF$_1$-strain mice (female, 8 to 10 weeks old) were killed by cervical dislocation, and the femurs were collected under sterile conditions. The bone marrow cells were flushed out from the femurs with α-medium, and formed into a single cell suspension by repeated aspiration with a 26-gauge needle fitted to a 1 ml-syringe. The cells were washed two times with α-medium by centrifugation at 200×G for 5 minutes and used in the following experiments.

(1) Effect of the dolichols on the differentiation and proliferation of the early erythrocytic progenitor cells (BFU-e)

In accordance with the method of Murphy et al. (In Vitro Aspects of Erythropoiesis, page 262, Sringer-Verlag, 1978), mouse bone marrow cells were plated at $2 \times 10^5$ nuclear cells into 1 ml of α-medium containing 1 unit of erythropoietin, 30% fetal bovine serum, 1% bovine serum albumin, 0.1 mM 2-mercaptoethanol and 0.8% methyl cellulose with 20 μg of dolichyl phosphate dispersed in 1 μl of dimethyl sulfoxide or 1 μl of dimethyl sulfoxide in a 35 mmφ tissue culture plate, and incubated at 37° C. in a humidified atmosphere of 5% carbon dioxide in air for 9 days. The number of burst colonies consisting of more than 500 erythroblasts derived from BFU-e in the tissue culture plate was scored with an inverted microscope. The experiment was carried out by 6 replica assays for each group, and the average number of the colonies formed was determined. The results are shown in Table 3, in the row of Run 1.

(2) Effect of the dolichols on the differentiation and proliferation of the late erythrocytic progenitor cells (CFU-e)

In accordance with the method of Murphy et al. mentioned above, mouse bone marrow cells were plated at $2.5 \times 10^4$ nuclear cells into 0.5 ml of α-medium containing 0.25 unit of erythropoietin, 30% fetal bovine serum, 1% bovine serum albumin, 0.1 mM 2-mercaptoethanol and 0.4% methyl cellulose with 10 μg of dolichol dissolved in 1 μl of ethanol, 10 μg of dolichyl phosphate dispersed in 0.5 μl of dimethyl sulfoxide, 1 μl of ethanol or 0.5 μl of dimethyl sulfoxide in a 16 mmφ tissue culture plate, and incubated at 37° C. in a humidified atmosphere of 5% carbon dioxide in air for 2 days. The number of cluster colonies consisting of 8 to 64 erythroblasts derived from CFU-e in the tissue culture plate was scored with an inverted microscope. The experiment was carried out by 6 replica assays for each group, and the average number of the colonies formed was determined. The results are shown in Table 3, in the rows of Runs 2 to 4.

(3) Effect of the dolichols on the differentiation and proliferation of granulocyte-macrophage progenitor cells (CFU-e)

In accordance with the method of Worton et al. [R. G. Worton et al., J. Cell Physiol., 74, 171 (1969)], mouse bone marrow cells were plated at $1 \times 10^5$ nuclear cells into 1 ml of α-medium containing 10% L cell-conditioned medium as source of colony stimulating factor, 20% fetal bovine serum and 0.8% methyl cellulose with 20 μg of dolichyl phosphate dispersed in 1 μl of dimethyl sulfoxide or 1 μl of dimethyl sulfoxide in a 35 mmφ tissue culture plate, and incubated at 37° C. in a humidified atmosphere of 5% carbon dioxide in air for 7 days. The number of colonies consisting of more than 50 cells (granulocyte colonies, macrophage colonies or their mixed colonies) derived from CFU-e was scored with an inverted microscope. The experiment was carried out by 6 replica assays for each group, and the average number of the colonies formed was determined. The results are shown in Table 3 in the row of Run 5.

TABLE 3

| Run | Hematopoietic progenitor cells | Dolichol tested | Number of colonies formed in the solvent-added control group (d) | Number of colonies formed in the dolichols-added group (d) | Percent increase (%) of colony formation (e) |
|---|---|---|---|---|---|
| 1 | BFU-e | Dolichyl phosphate (a) 20 μg/ml | 73.7 ± 3.4 | 99.5 ± 2.4 | +35.0 |
| 2 | CFU-e | Dolichol (b) 20 μg/ml | 124.2 ± 2.7 | 151.0 ± 2.2 | +21.6 |
| 3 | CFU-e | Dolichol (c) (n = 15) 20 μg/ml | 246.0 ± 5.0 | 293.0 ± 6.2 | +19.1 |
| 4 | CFU-e | Dolichyl phosphate (a) 20 μg/ml | 124.7 ± 2.9 | 166.7 ± 2.4 | +33.7 |

TABLE 3-continued

| Run | Hematopoietic progenitor cells | Dolichol tested | Number of colonies formed in the solvent-added control group (d) | Number of colonies formed in the dolichols-added group (d) | Percent increase (%) of colony formation (e) |
| --- | --- | --- | --- | --- | --- |
| 5 | CFU-c | Dolichyl phosphate (a) 20 g/ml | 256.8 ± 4.3 | 295.3 ± 4.9 | +15.0 |

(a) Synthesized in accordance with Referential Example 3.
(b) Obtained in accordance with Referential Example 1.
(c) Separated in accordance with Referential Example 2.
(d) Mean ± S.E. obtained from the 6 replica assays
(e) Percent increase (%) in the number of colonies formed in the dolichol-added group based on the number of colonies formed in the solvent-added control group (4) Erythropoiesis enhancing effect of the dolichols in vivo Phenylhydrazine was administered to normal mice and hereditarily anemic mice to induce severe hemolytic anemia. Then, the rate of erythropoiesis during recovering of anemia was determined by measuring the rate of radioactive iron ($^{59}$Fe) incorporation into newly formed red blood cells [P. M. Cotes, D. R. Bangham, Nature (London), 191, 1067 (1961)]. The testing method and results are described below.

Run 6

Phenylhydrazine hydrochloride (60 mg/kg) dissolved in normal saline solution was subcutaneously injected into BDF$_1$-strain mice (6 weeks old, female) three times, namely on the 1st, 2nd and 4th day of the experiment to produce phenylhydrazine-induced anemic mice. Dolichol in a dose of 250 mg/kg (25 mg of dolichol was emulsified in 1 ml of a 1% aqueous solution of sodium carboxymethyl cellulose; 0.2 ml/20 g of the body weight) was intraperitoneally administered to the mice twice, namely on the 1st and 2nd day. Mice in a control group was rendered anemic by injection of phenylhydrazine, and a 1% aqueous solution of sodium carboxy methyl cellulose was intraperitoneally administered (0.2 ml/20 g of the body weight) on the 1st and 2nd day. On the 4th day, ($^{59}$Fe) ferric citrate (0.5 μCi/mouse) was intraperitoneally administered to the mice in each group. On the 6th day, 0.5 ml of the whole blood was taken from each mouse, and the radioactivity of $^{59}$Fe incorporated into the whole blood during the period of 48 hours was measured by an auto-gamma-counter. The experiment was carried out on 6 mice in each of the test group and the control group. By assuming that the amount of the whole blood of each mouse was 7% of the body weight, the $^{59}$Fe incorporation rates were calculated in accordance with the following equation and averaged.

$$^{59}\text{Fe incorporation rate (\%)} = \frac{\left(\begin{array}{c}\text{Radioactivity}\\\text{(cpm) in 0.5 ml}\\\text{of the whole}\\\text{blood}\end{array}\right) \times \left(\begin{array}{c}\text{Body}\\\text{weight}\\\text{(g)}\end{array}\right) \times \frac{2 \times 7}{100}}{\text{(Radioactivity (cpm) of the injected } ^{59}\text{Fe)}}$$

The results are shown in Table 4, in the row of Run 6.

Run 7

Dolichyl phosphate in a dose of 250 mg/kg (0.2 ml of an emulsion obtained by emulsifying 25 ml of dolichyl phosphate and 25 mg of sesame oil in 1 ml of a 1% aqueous solution of sodium carboxymethyl cellulose per 20 g of the body weight) was intraperitoneally administered to hereditarily anemic WBB$_6$F$_1$-W/Wv-strain mice (6 weeks old, female) on the 1st day of the experiment. A 1% aqueous solution of sodium carboxymethyl cellulose was intraperitoneally administered (0.2 ml/20 g of body weight) to a control group. On the 2nd day, the mice in each group were subcutaneously injected with phenylhydrazine hydrochloride in a dose of 60 mg/kg. On the 3rd day, ($^{59}$Fe) ferric citrate was intraperitoneally administered (0.5 μCi/mouse). On the 5th day, 0.5 ml of the whole blood was taken from each mouse, and the $^{59}$Fe incorporation rates during the period of 48 hours were measured as in Run 6. The experiment was carried out on 6 mice in each group, and the average value of the incorporation rates was calculated. The results are shown in Table 4, in the row of Run 7.

TABLE 4

| | | $^{59}$Fe incorporation rate (%) | | |
| --- | --- | --- | --- | --- |
| | Dolichol tested | Control group | Dolichol administered group | Erythropoiesis enhancing ratio (%) (***) |
| Run 6 | Dolichol (*) 250 mg/kg twice | 48.2 | 50.2 | +4.2 |
| Run 7 | Dolichyl phosphate (**) 250 mg/kg once | 21.4 | 23.1 | +7.9 |

(*) Obtained in accordance with Referential Example 1.
(**) Synthesized in accordance with Referential Example 3.
(***) Percent increase of the $^{59}$Fe incorporation rate of the dolichol administered group based on the $^{59}$Fe incorporation rate of the control group The dolichols are free from side-effects that are seen in the aforesaid adrenergic agonist or steroid hormones, and have little toxicity. Hence, they are very advantageous are pharmaceuticals. The absence of side effects can be confirmed by the following experiment in which the dolichol synthesized in Referential Example 1 given hereinafter was used.

Side-effects

Since the dolichol is a water-insoluble oily liquid, it was used as a solution in sesame oil in the case of oral administration, and as a suspension in a nonionic surfactant (HCO-60, a trade name for a product of Nikko Chemical Co., Ltd.) in the case of intraperitoneal administration and in an in vitro test in the following experiment.

In the following experiment, ddY-strain male mice, Wistar-strain male rats (Shizuoka Laboratory Animal Center), Japanese white male rabbits (Carely) and Hartley-strain male guinea pigs (Clea Japan Inc.) were used. The animals were kept under conditions including a temperature of 23±1° C., a humidity of 55±10%, an illuminating time (7:00 am to 9.00 pm) and 15 ventilations per hour. The mice and rats were fed with solid feeds MF (a product of Oriental Yeast Co., Ltd.) and the guinea pigs and rabbits were fed with solid feeds GM-3 and RM-1 (Funabashi Farm Co.). They were allowed to take tap water freely. The animals were preliminarily kept for more than one week, and those which were healthy in general conditions were used in the experiments.

(a) Neuropharmacological test using mice ddY-strain male mice, 6 per group, were used, and their changes in behavior, nervous symptoms, autonomic nervous symptoms and toxic symptoms were observed, analyzed and recorded in accordance with the Irwin's method of observation. Dolichol was intraperitoneally administered in a dose of 150, 300 and 600 mg/kg, respectively.

In the above doses of dolichol, no effect was observed on the behaviors, nervous symptoms, autonomic nervous symptoms and toxic symptoms of the mice.

(b) Test on peripheral action using extracted organs i. Sample of the extracted ileum of guinea pigs Hartley-strain male guinea pigs (350 to 400 g), 3 per group, were used, and the extracted ileum samples were suspended in Tyrode solution at 32° C. through which air was introduced. The contraction of the ileum was recorded on an ink-writing oscillograph (EMP-3004, Nippon Photoelectric Co. through an isotonic transducer (TD-112S, Nippon Photoelectric Co.). The direct action of dolichol and the antagonistic action of dolichol against acetylcholine, histamine and nicotine in a concentration of $10^{-6}$ g/ml, $10^{-5}$ g/ml, and $10^{-4}$ g/ml, respectively, were examined.

As a result, in concentrations of up to $10^{-4}$ g/ml, dolichol was found to have no direct action on the extracted ileum samples of guinea pigs nor any antagonistic action against the aforesaid agonists.

ii. Extracted spermiduct samples of rats

Wistar-strain male rats (180 to 200 g), 3 per group, were used. The extracted spermiduct samples were suspended in Locke-Ringer solution at 32° C. The contraction of the spermiduct was recorded by the same method as in the preceding section. The direct action of dolichol and the antagonistic action of dolichol against noradrenalin in a concentration of $10^{-6}$ g/ml, $10^{-5}$ g/ml and $10^{-4}$ g/ml, respectively, were examined.

As a result, dolichol was found to have no direct action on the extracted spermiduct samples of rats nor any antagonistic action against noradrenalin in concentrations of up to $10^{-4}$ g/ml.

iii. Extracted atrium samples of guinea pigs

Hartley-strain male guinea pigs (350–400 g), 3 per group, were used. Atrium samples composed of the left and right atria were prepared, and suspended in Krebs-Henseleit solution at 30° C. through which a gaseous mixture composed of 95% of $O_2$ and 5% of $CO_2$ was introduced. The contraction of the atria was recorded on an ink-writing oscillograph (EMP-3004, Nippon Photoelectric Co.) through an FD pick-up (TB-611T, Nippon Photoelectric Co.). The inotropic action and chronotropic action of dolichol in a concentration of $10^{-6}$ g/ml, $10^{-5}$ g/ml and $10^{-4}$ g/ml, respectively, were examined.

As a result, dolichol was found to have no inotropic nor chronotropic action against the ex tracted atrium samples of guinea pigs.

iv. Extracted trachea samples of guinea pigs

Hartley-strain male guinea pigs (350–400 g), 3 per group, were used. The extracted trachea was suspended in Locke-Ringer solution at 37° C. through which air was introduced. The contraction of the trachea was recorded in the same way as in the case of the extracted ileum. The direct action of dolichol and the antagonistic action of dolichol against isoproterenol were examined in a concentration of $10^{-6}$ g/ml, $10^{-5}$ g/ml and $10^{-4}$ g/ml, respectively.

As a result, dolichol was found to have no direct action on the extracted trachea samples nor antagonistic action against isoproterenol in concentrations of up to $10^{-4}$ g/ml.

(c) Effect on the blood coagulation system in rats

Wistar-strain male rats (180–210 g), 6 per group, were used. Two hours after administration of dolichol to rats, the blood was taken from the abdominal main vein of the rats, and the prothrombin time was measured by the Quick's one-step method.

The prothrombin time tended to become longer in groups to which dolichol was administered in a dose of 150, 300 and 600 mg/kg, respectively, than in a control group, but no significant difference was noted.

(d) Blood sugar lowering action in rats

Wistar-strain male rats (180–210 g), 6 per group, were used. Two hours after administration of dolichol to the rats, the blood was taken from the abdominal main vein of the rats, and the blood sugar level was measured by the glucose-oxidase method.

In comparison with a control group, no significant difference was noted in groups to which dolichol was administered in doses of 150, 300 and 600 mg/kg.

(e) Diuretic action in rats

Wistar-strain male rats (80–90 g), 6 per group, were used. Immediately after administration of dolichol to the rats, normal saline solution was orally administered to the rats in a dose of 2.5 ml/100 g. The rats were put singly in metabolic cages. Urine was taken 6 hours after administration of dolichol, and its amount was measured.

In comparison with a control group, no significant difference was noted in groups to which dolichol was administered in doses of 150, 300 and 600 mg/kg.

(f) Analgesic action in mice (acetic acid writhing method)

ddY-strain male mice (27–30 g), 6 per group, were used. One hour after administration of dolichol to the mice, 0.6% acetic acid was intraperitoneally administered to the mice in a dose of 0.1 ml/10 g. The mice were observed for 10 minutes after 10 minutes from the administration of acetic acid. The inhibitory action on acetic acid writhing was thus examined.

In comparison with a control group, no significant difference was noted in groups to which dolichol was administered in doses of 150, 300 and 600 mg/kg.

(g) Reserpine antagonistic action in mice ddY-strain male mice (27–30 g), 6 per group, were used. Reserpine was intraperitoneally administered to the mice in a dose of 4 mg/kg, and 3 hours later, dolichol was administered to the mice. One hour after the administration of dolichol, the degree of blepharoptosis in the mice was observed and recorded in accordance with the Rubin's standards of evaluation (0: normal opening of the eyes, 1: ¼ blepharoptosis, 2: ½ blepharoptosis, 3: ¾ blepharoptosis, 4: complete blepharoptosis).

In comparison with a control group, no antagonistic action against reserpine-induced blepharoptosis was noted in groups to which dolichol was administered in doses of 150, 300 and 600 mg/kg.

(h) Anticonvulsive action (action against maximal electroshock seizure) in mice ddY-male mice (27-30 g), 6 per group, were used. One hour after administration of dolichol to the mice, an electric current was passed through the corneas of the mice under conditions of 40 mA, 0.4 msec, 50 Hz and 0.5 sec, and the time of duration of tonic extension (T. E.) was measured.

In comparison with a control group, no significant difference was noted in groups to which dolichol was administered in doses of 150, 300 and 600 mg/kg.

(i) Local anesthetic action in guinea pigs

Hartley-strain male guinea pigs (370-440 g), 3 per group, were used. Dolichol was dropped in a concentration of 0.001%, 0.01% and 0.1%, respectively, into the eyes of the guinea pigs. Before administration and 1, 2, 3, 4, 5, 10, 15 and 20 minutes after administration, corneal reflex by frey irritation hairs was examined.

In concentrations of up to 0.1% of dolichol, there was no disappearance of corneal reflex. Thus, no local anesthetic action was observed.

Acute toxicity (1) Dolichol synthesized in Referential Example 1 below was used as a solution in sesame oil in the case of oral administration, or as a suspension in HCO-60 (a trade name for a nonionic surfactant made by Nikko Chemical Co., Ltd.) in the case of intraperitoneal administration.

ddY-strain mice (21-27 g), 6 per group, were used. Dolichol was administered to the mice in a dose of 5,000 mg/kg orally, or 1,000 mg/kg intraperitoneally on the 1st day of the test, and the mice were then observed for toxic symptoms and mortality for seven days. The body weights of the mice were measured before administration and on the 1st and 7th days. Control groups were each given sesame oil or HCO-60, and observed and weighed in the same way as in the case of the groups to which dolichol was administered. On the 7th day, all the mice were dissected and visually observed. There was no case of death in all of the mice tested, and in regard to changes in body weight, no sigificant difference was noted in groups to which dolichol was administered in comparison with the control groups. No abnormality was noted in dissection on the 7th day.

(2) Dolichyl phosphate synthesized in Referential Example 3 below was dissolved in the same amount of sesame oil, and added to a 1% aqueous solution of sodium carboxy methyl cellulose so that the concentration of dolichyl phosphate reached 5% V/V. The resulting emulsion was used in the test.

$BDF_1$-strain mice (20-23 g, female), 6 per group, were used. Dolichyl phosphate was administered intraperitoneally in doses of 1000 mg/kg and 2000 mg/kg, and on the 2nd day of the administration, the mice were observed for mortality. There was no case of death in all of the mice tested.

As stated hereinabove, the dolichols have the effect of enhancing differentiation and proliferation of hematopoietic progenitor cells with little side-effects and toxicity, and are useful as drugs for humans and other animals in the prevention, therapy and treatment of various diseases induced by decrease of differentiation and proliferation of hematopoietic progenitor cells, for example, various cases of aplastic anemia occurring hereditarily or inhereditarily, such as geriatric anemia attributed to the decrease of hematopoietic function, congenital aplastic anemia and familial aplastic anemia, and hematopoietic impediments attributed to the administration of carcinostatic drugs or radioactive irradiation for cancer therapy.

In using the dolichols for the aforesaid diseases, their doses may be varied widely depending upon the route of administration, the condition, body weight, age and sex of a patient, the judgement of a physician who treats the patient, etc. Generally, the doses are 0.05 to 1,000 mg/kg/day, preferably 0.1 to 100 mg/kg/day, more preferably 0.2 to 50 mg/kg/day, either at a time or in several divided portions daily.

The dolichols may be administered orally or parenterally (e.g., intravenously, intraarterially, intramuscularly, intraperitoneally, intramedullarily, intrarectally).

The dolichols may be formulated into forms suitable for oral administration, for example tablets, granules, powders, coated tablets, hard capsules, elastic capsules and syrups, or into forms suitable for injection or intravenous drip infusion such as suspension, solutions, or oily or aqueous emulsions.

The dolichols may be formulated into a pharmaceutical composition or agent using various pharmaceutically acceptable liquid or solid diluents or carriers. Examples of such diluents or carriers include syrup, gum arabic, gelatin, sorbitol, tragacanth, polyvinyl pyrrolidone, magnesium stearate, talc, polyethylene glycol, silica, lactose, sucrose, corn starch, calcium phosphate, glycine, potato starch, calcium carboxymethyl cellulose, sodium laurylsulfate, water, ethanol, glycerol, mannitol and a phosphate buffer.

The pharmaceutical composition or agent of this invention may, if required, further contain other adjuvants customarily useful in the field of pharmaceutical formulation, such as coloring agents, flavors, corrigents, antiseptics, dissolution aids, suspending agents and dispersing agents.

The pharmaceutical composition or agent may be in unit dosage forms such as the tablets, capsules, coated tablets and ampoules mentioned above, or may be in a form contained in a multiunit dosage receptacle.

The pharmaceutical composition or agent, depending upon its form, etc., may contain the dolichols in a concentration of generally 0.01 to 50% by weight, preferably 0.1 to 20% by weight.

The following examples illustrate the present invention further.

REFERENTIAL EXAMPLE 1

Dolichol was synthesized in accordance with the method described in EP-A-0054753.

One hundred kilograms (undried weight) of yellowed leaves of *Ginkgo biloba* collected in November in Kurashiki City, Japan were dried with hot air at about 40° C. for 10 hours, and immersed in 800 liters of chloroform at room temperature (about 15° C.) for 1 week. Chloroform was evaporated from the extract, and 50 liters of hexane was added to the resulting concentrate. The insoluble components were removed by filtration, and the filtrate was concentrated. The concentrate was chromatographed on a column of silica gel using a mixture of hexane/ethyl acetate as a developing solvent. A fraction having an Rf of 0.52 in silica gel thin-layer chromatography using a mixture of hexane/ethyl acetate (9/1 by volume) (developed 10 cm using TLC plate silica $60F_{254}$, precoated, thickness 0.25 mm, made by Merck Co.) was separated, and about 275 g of a liquid was obtained. The liquid was heated together with 2 liters of methanol, 200 ml of water and 150 g of potassium hydroxide at 65° C. for 2 hours, and 2 liters of hexane was added. The extracted organic layer was washed with water five times, and dried over anhydrous magnesium sulfate. The solvent was evaporated, and the resulting liquid was purified by silica gel column chromatography using a mixture of hexane and ethyl acetate as a developing solvent to obtain about 227 g of polyprenol. This compound, 25 g of pyridine and 50 g of acetic anhydride were dissolved in 5 liters of hexane, and the solution was stirred at room temperature for 12 hours. The resulting mixture was washed with a saturated aqueous solution of sodium chloride, dried over anhydrous magnesium sulfate, and concentrated to give 228 g of polyprenyl acetate.

A three-necked flask purged with argon was charged with 3.16 g (130 millimoles) of small fragments of magnesium, 5 ml of anhydrous tetrahydrofuran and 0.8 ml of 1,2-dibromoethane, and they were heated by a dryer until vigorous bubbling occurred. A solution of 25.1 g (100 millimoles) of (R)-2-[4-bromo-3-methylbutoxy]-tetrahydro-2H-pyran ($[\alpha]_D^{20} = -3.61°$, c=4.0, $CHCl_3$) in 30 ml of anhydrous tetrahydrofuran was added to the activated magnesium at such a speed that the solvent just boiled. After the addition, the mixture was stirred at 70° C. for 15 minutes, and 600 ml of anhydrous tetrahydrofuran was added to form a Grignard solution.

Separately, a three-necked flask purged with argon was charged with a solution of 64.2 g (50 millimoles) of the polyprenyl acetate prepared above in 150 ml of anhydrous tetrahydrofuran and 200 ml of an anhydrous tetrahydrofuran solution of $Li_2CuCl_4$ (0.1M). The Grignard solution prepared above was added dropwise to the solution at 0° C. over the course of 4 hours, and the reaction was continued at 0° C. for 4 hours. A saturated aqueous solution of ammonium chloride was added to the reaction mixture to perform hydrolysis, and the product was extracted with ether. The ethereal layer was washed with a saturated aqueous solution of sodium chloride and dried over anhydrous magnesium sulfate. The solvent was then evaporated by a rotary evaporator to obtain a pale yellow liquid product. The product was dissolved in 400 ml of hexane, and 1.3 g (5 millimoles) of pyridine p-toluenesulfonate and 200 ml of ethanol were added. The solution was heated with stirring at 55° C. for 3 hours. The reaction mixture was cooled to room temperature, neutralized with 2.5 g of sodium carbonate, washed with a saturated aqueous solution of sodium chloride, and dried over anhydrous magnesium sulfate. The solvent was evaporated. The remaining liquid product was heated at 150° C. and 0.5 torr for 30 minutes to remove low-boiling components. The residue was purified by silica gel column chromatography using a mixture of hexane and ethyl acetate as a developing solvent to give 56.8 g of a colorless transparent liquid product. This product was determined to be the dolichol of formula (I) by IR and NMR analyses. The product was subjected to high-performance liquid chromatography using $\mu$-Bondapak-$C_{18}$ (silica gel surface-treated with a $C_{18}$ hydrocarbon compound) as a filler, acetone/methanol (90/10 by volume) as a developing solvent and a differential refractometer as a detector. The proportions of the areas of the individual peaks in the resulting chromatogram were determined, and defined as the contents of the compounds of formula (I) having varying n values as shown below.

| n = 12 | 1.2% |
|---|---|
| 13 | 6.7 |
| 14 | 24.6 |
| 15 | 40.4 |
| 16 | 20.0 |
| 17 | 5.9 |
| 18 | 1.2 |

REFERENTIAL EXAMPLE 2

Ten grams of the dolichol of formula (I) having n distributed from 12 to 18 synthesized by the method of Referential Example 1 was separated into the individual components having varying n values by using a semi-fractionation type of high-performance liquid chromatographic column ($C_{18}$ type) RP18-10 (a product of Merck Co.) with a mixed solvent of acetone and methanol (90/10 by volume) as a developing solvent. The amounts of these components were as follows:

| n = 12 | 0.1 g |
|---|---|
| 13 | 0.65 g |
| 14 | 2.6 g |
| 15 | 4.0 g |
| 16 | 1.9 g |
| 17 | 0.6 g |
| 18 | 0.1 g |

$^1$H-NMR, $^{13}$C-NMR and FD-MASS spectral analyses led to the determination that these separated components had the chemical structures corresponding to n values of 12 to 18 in formula (I).

REFERENTIAL EXAMPLE 3

Conversion to dolichyl phosphate:

The dolichol synthesized in Referential Example 1 was converted to the phosphate in accordance with the method of L. L. Danilov et al. (Febs Letters, Vol. 131, page 310, 1981).

Triethylamine (2.87 ml) was added to a solution of 1.92 ml of phosphorus trichloride in 75 ml of hexane, and the mixture was stirred. A solution of 5 g of the dolichol synthesized in Referential Example 1 in 75 ml of hexane was added dropwise at room temperature, and the mixture was stirred for 30 minutes. The reaction mixture was poured into a mixture of acetone/methanol/water (88/10/2 by volume), and the mixture was stirred overnight at room temperature. The mixture was then put in a separating funnel, and the upper layer was separated, washed with a saturated aqueous solution of sodium chloride, and dried over anhydrous magnesium sulfate. The solvent was evaporated under reduced pressure to give a yellow liquid product. The product was chromatographed on a column of DEAE-cellulose (acetate-type cellulose ion exchanger, 3.5 cm id×12 cm) using a developing solvent obtained by adding a small amount of ammonium acetate to a mixture of chloroform/methanol (2/1 by volume) to obtain a fraction containing dolichyl phosphate. The fraction was subjected to gel filtration using Sephadex LH-20 (dextran gel, 40 g) and a chloroform/methanol (2/1 by volume) developing solvent to remove ammonium acetate. The resulting solution was concentrated to give 3.0 g of dolichyl phosphate. When this product was analyzed by NMR, the signal ($\delta$=3.66) assigned to $-\underline{CH_2}OH$ of the starting dolichol disappeared, and a signal ($\delta$=3.90) assigned to

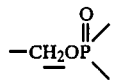

appeared, and otherwise, nearly the same signals as the starting material were observed. This led to the determination that the resulting compound is dolichyl phosphate.

REFERENTIAL EXAMPLE 4

Conversion to dolichyl acetate:

The dolichol (13.1 g; 10 millimoles) synthesized in Referential Example 1 was dissolved in 100 ml of anhydrous methylene chloride, and 3.2 g (40 millimoles) of pyridine and 50 mg of 4-dimethylaminopyridine were added. With stirring under ice cooling, 2.04 g (20 millimoles) of acetic anhydride was added dropwise. The mixture was stirred at room temperature for 30 minutes and poured into water. The mixture was extracted with methylene chloride. The organic layer was washed with dilute hydrochloric acid and water, and dried over anhydrous magnesium sulfate. The solvent was evaporated under reduced pressure to give a yellow liquid product. The product was purified by silica gel column chromatography using hexane/ethyl acetate (99/1 by volume) as a developing solution to obtain a colorless transparent liquid product (12.2 g). NMR analysis of this product showed that the signal ($\delta=3.66$) assigned to $-\underline{CH_2}OH$ of the starting dolichol disappeared, and signals ($\delta=4.04$ and 1.97) assigned to

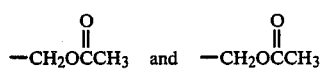

appeared, and otherwise, nearly the same signals as the starting material were observed. IR analysis showed the following results. 3030, 2950, 2910, 2845, 1740, 1660, 1440, 1370, 1230, 1020, 830 cm$^{-1}$.

From the foregoing results of the analyses, the product was determined to be dolichyl acetate.

REFERENTIAL EXAMPLE 5

Conversion to dolichyl palmitate:

The dolichol (1.31 g; 1 millimole) obtained in Referential Example 1 was dissolved in 2 ml of anhydrous diethyl ether, and 80 mg (1 millimole) of pyridine was added. With stirring at room temperature 275 mg (1 millimole) of palmitoyl chloride was added. The mixture was stirred for 3 hours, and poured into water. The mixture was extracted with diethyl ether. The organic layer was washed with dilute hydrochloric acid and water, and dried over anhydrous magnesium sulfate. The solvent was evaporated under reduced pressure to obtain 1.4 g of a yellow liquid product. The product was purified by silica gel column chromatography using hexane as a developing solvent to obtain 1.3 g of a colorless transparent liquid product. NMR analysis of the product showed that the signal ($\delta=3.66$) assigned to $-\underline{CH_2}OH$ of the starting dolichol disappeared, and signals ($\delta=4.04$ and 1.28) assigned to

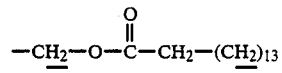

were observed. IR analysis showed the following results. 3040, 2970, 2935, 2860, 1740, 1665, 1450, 1380, 1170 and 830 cm$^{-1}$.

The above results led to the determination that the product was dolichyl palmitate.

EXAMPLE 1

Formulation of an injectable preparation:

| | |
|---|---|
| Dolichol obtained in Referential Example 1 | 10 mg |
| Polyoxyethylene hardened castor oil | 70 mg |
| Sorbitan trioleate | 5.0 mg |
| Propylene glycol | 20 mg |
| Water for injection | about 1 ml |

Polyoxyethylene hardened castor oil and sorbitan trioleate were weighed and dissolved by heating. The dolichol obtained in Referential Example 1, which had been separately weighed, was added. The mixture was rapidly stirred under heat for a while. After cooling, propylene glycol and water for injection were added, and the total amount of the mixture was adjusted to 1 ml. The mixture was then filtered in the same manner as used in the conventional preparation of injectable preparations, and filled into 1 ml brown ampoules. Nitrogen was sealed into the ampoules. Sterilization was carried out by a flowing steam method at 100° C. for 40 minutes.

EXAMPLE 2

Formulation of tablets:

| | |
|---|---|
| Dolichol obtained in Referential Example 1 | 10 g |
| Bees wax | 1 g |
| Hydroxypropyl cellulose | 3 g |
| Water | 30 ml |
| Crystalline cellulose | 30 g |
| Lactose | 30 g |
| Corn starch | 20 g |
| Calcium carboxymethyl cellulose | 5 g |

The dolichol obtained in Referential Example 1, bees wax and hydroxypropyl cellulose were weighed, and water was added. The mixture was heated to about 70° C. to form an emulsion. The crystalline cellulose, lactose and corn starch were mixed, and the emulsion was added to cause adsorption of the mixture. After drying, the particles were adjusted in size, and mixed with calcium carboxymethyl cellulose. The resulting mixture was tableted into tablets each having a diameter of 6 mm and a thickness of 3.3 mm and weighing 100 mg.

EXAMPLE 3

Formulation of an injectable preparation:

| | |
|---|---|
| Dolichol (n = 15) obtained in Referential Example 2 | 1 g |
| Polyoxyethylene hardened castor oil | 7 g |
| Propylene glycol | 10 g |
| Glucose | 2.5 g |
| Water for injection | about 100 ml |

The dolichol (n=15) obtained in Referential Example 2, polyoxyethylene hardened castor oil and propylene glycol were weighed, and heated to form a solution. The solution was rapidly stirred for a while. After cooling, water for injection was added to adjust the total amount to 100 ml. The solution was filtered in the same manner as used for the conventional making of injectable preparations, and filled in 1 ml brown ampoules. Nitrogen was then sealed into the ampoules. Sterilization was carried out by a flowing steam method at 100° C. for 40 minutes.

EXAMPLE 4

Formulation of an injectable preparation:

| | |
|---|---|
| Dolichyl phosphate obtained in Referential Example 3 | 1 g |
| Polyoxyethylene sorbitan monoleate (Tween-80) | 5 g |
| Glycerol triester of butyric acid (tributyrin) | about 100 ml |

Dolichyl phosphate obtained in Referential Example 3 and polyoxyethylene sorbitan monoleate were mixed, and the mixture was diluted with tributyrin to a volume of 100 m. The solution was filtered in the same manner as used in the conventional making of injectable preparations, and filled in 1 ml brown ampoules. Nitrogen was then sealed into the ampoules. Sterilization was carried out by a flowing steam method at 100° C. for 40 minutes.

EXAMPLE 5

Formulation of a powder:

| | |
|---|---|
| Dolichol obtained in Referential Example 1 | 5 g |
| Microcrystalline cellulose | 40 g |
| Corn starch | 55 g |

Dolichol obtained in Referential Example 1 was dissolved in acetone, and the solution was adsorbed on microcrystalline cellulose and dried. The mixture was mixed with corn starch to prepare a powder containing 1/20 of the active ingredient (dolichol).

EXAMPLE 6

Formulation of capsules:

| | |
|---|---|
| Dolichol obtained in Referential Example 1 | 5 g |
| Microcrystalline cellulose | 80 g |
| Corn starch | 20 g |
| Lactose | 22 g |
| Polyvinyl pyrrolidone | 3 g |

The above ingredients were granulated, and filled into 1,000 hard gelatin capsules. Each capsule contained 5 mg of dolichol.

What we claim is:

1. A method for enhancing differentiation and proliferation of hematopoietic progenitor cells in a mammal, which comprises administering to the mammal an effective amount of a compound of the formula

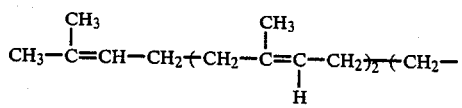

wherein

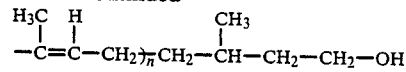

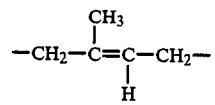

is a trans-isoprene unit,

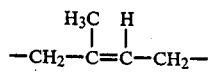

is a cis-isoprene unit, and n is an integer of from 12 to 18, or a pharmaceutically acceptable ester thereof.

2. A method for enhancing differentiation and proliferation of hematopoietic progenitor cells in a mammal, which comprises administering to the mammal an effective amount of a compound of the formula

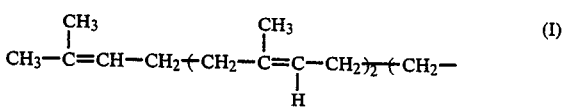

wherein

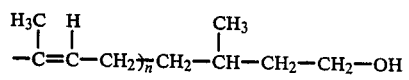

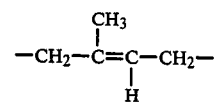

is a trans-isoprene unit,

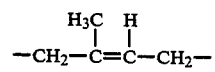

is a cis-isoprene unit, and n is an integer of from 12 to 18, or a pharmaceutically acceptable ester thereof selected from the group consisting of a fatty acid ester, a phosphoric acid ester and a monomannosyl phosphate ester.

3. A method for enhancing differentiation and proliferation of hematopoietic progenitor cells in a mammal, which comprises administering to the mammal an effective amount of a composition containing a mixture of compounds of the formula

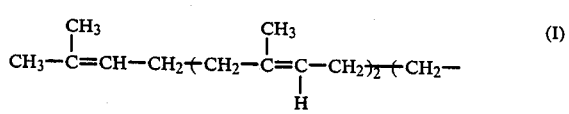

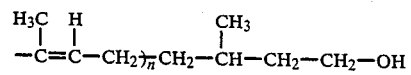

wherein

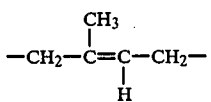

is a trans-isoprene unit,

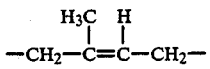

is a cis-isoprene unit, and n is an integer of from 12 to 18, or a pharmaceutically acceptable ester thereof selected from the group consisting of a fatty acid ester, a phosphoric acid ester and a monomannosyl phosphate ester, wherein the distribution of n in the compounds of formula (I) or the esters thereof is within the following ranges:

| n in formula (I) | weight % based on weight of said mixture |
| --- | --- |
| 12 | 0–6 |
| 13 | 4–17 |
| 14 | 20–35 |
| 15 | 30–50 |
| 16 | 10–25 |
| 17 | 2–10 |
| 18 | 0–5. |

4. The method of claim 3 wherein the composition is administered orally or parenterally.

5. The method of claim 3 wherein the compounds are administered in a total dose of 0.05 to 1,000 mg/kg/day.

6. The method of claim 3 wherein the distribution of n in the compounds of formula (I) or the esters thereof is within the following ranges:

| n in formula (I) | weight % based on weight of said mixture |
| --- | --- |
| 12 | 0.1–6 |
| 13 | 5–14 |
| 14 | 23–32 |
| 15 | 32–47 |
| 16 | 11–20 |
| 17 | 2–6 |
| 18 | 0.1–2. |

7. The method of claim 2 wherein the compound is administered orally or parenterally.

8. The method of claim 2 wherein the compound is administered in a dose of 0.05 to 1,000 mg/kg/day.

* * * * *